United States Patent

Koch et al.

[11] Patent Number: 5,567,707
[45] Date of Patent: Oct. 22, 1996

[54] ACRONYCINE ANALOGUES

[75] Inventors: Michel Koch, La Celle Saint Cloud; François Tillequin, Paris, both of France; Alexios-Leandros Skaltsounis, Athenes, Greece; Yves Rolland, Vanves, France; Alain Pierre, Marly-le-Roi, France; Ghanem Atassi, Saint-Cloud, France

[73] Assignee: Adir et Compagnie, Courbevoie, France

[21] Appl. No.: 389,798

[22] Filed: Feb. 16, 1995

[30] Foreign Application Priority Data

Feb. 17, 1994 [FR] France ................... 94 01806

[51] Int. Cl.⁶ .................................. C07D 491/04
[52] U.S. Cl. .................. 514/280; 514/285; 546/48; 546/62
[58] Field of Search ................. 514/280, 285, 514/279; 546/62, 48

[56] References Cited

U.S. PATENT DOCUMENTS

| | | | |
|---|---|---|---|
| 3,621,041 | 11/1971 | Kwok | 546/62 |
| 3,624,087 | 11/1971 | Beck | 546/62 |
| 3,657,249 | 4/1972 | Booher et al. | 546/62 |
| 3,673,163 | 6/1972 | Walkling | 514/285 |
| 3,715,359 | 6/1973 | Sullivan | 546/62 |
| 3,943,137 | 3/1976 | Higuchi et al. | 546/62 |

OTHER PUBLICATIONS

Mitaku et al. Chemical Abstr vol. 109 entry 129396 (1988).
Drummond et al. Chem. Abstr vol. 47 entry 3862 b (1953).

*Primary Examiner*—Donald G. Daus
*Attorney, Agent, or Firm*—The Firm of Gordon W. Hueschen

[57] ABSTRACT

Compounds of formula (I):

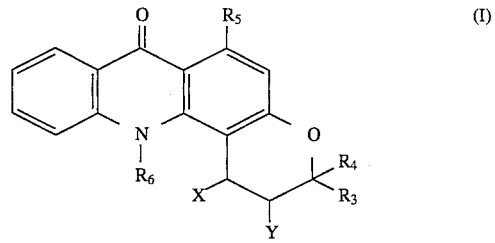

wherein $R_3$, $R_4$, $R_5$, $R_6$, X and Y are defined in the description.

Those compounds are used therapeutically in the treatment of cancerous tumours.

5 Claims, No Drawings

ACRONYCINE ANALOGUES

The present invention relates to new acronycine analogues, a process for their preparation, and pharmaceutical compositions containing them.

Acronycine is an alkaloid that was first isolated in 1948; its anti-tumour properties were demonstrated in experimental models in 1966 by G. H. Svoboda et al. (*J. Pharmaceut. Sci.*, 55 (8), (1966), 758–768).

Clinical studies carried out with that product by J. H. Scarffe et al. (*Cancer Treat. Rep.*, 67 (1), (1983), 93–94) gave little response, probably because of the insolubility of acronycine, which prevented administration by the intravenous route, and because of the poor bioavailability of that product when administered orally.

However, the works of G. H. Svoboda et al. (*Lloydia*, 29 (3), (1966), 206–244) demonstrated the broad spectrum of activity of acronycine in experimental models and especially against solid tumours.

The Applicant has recently discovered new acronycine analogues that are more active and more powerful than acronycine and, in particular, are more soluble, thus rendering possible administration by the intravenous route.

The present invention relates more particularly to compounds of formula (I):

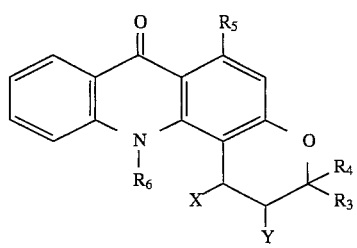

wherein:

X represents —O—$R'_1$ and Y represents

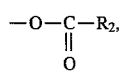

or X represents

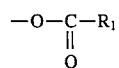

and Y represents

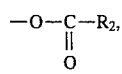

or X and Y together form the group

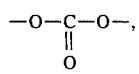

or X and Y together form the group

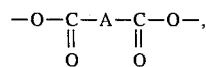

$R_1$ and $R_2$, which are the same or different, each represents, independently of the other, a hydrocarbon radical having 1 to 6 carbon atoms inclusive in straight or branched chain and being optionally substituted by one or more groups selected from hydroxy, halogen, nitro, amino, alkoxy and acyl, $R'_1$ is selected from hydrogen and $R_1$ A is selected from a valency bond and a divalent hydrocarbon group optionally having one or more unsaturations and having 1 to 6 carbon atoms inclusive in straight or branched chain, and which is optionally substituted by one or more groups selected from hydroxy, halogen, nitro, amino, alkoxy and acyl, $R_3$, $R_4$ and $R_6$, which are the same or different, are each selected, independently of the others, from hydrogen and alkyl, $R_5$ is selected from hydrogen, hydroxy and alkoxy, the terms "alkyl", "alkoxy" and "acyl" being understood to designate groups having 1 to 6 carbon atoms inclusive in straight or branched chain and optionally having one or more unsaturations, and which are optionally substituted by one or more groups selected from hydroxy, halogen, nitro, amino, alkoxy and acyl, their possible enantiomers, diastereoisomer, N-oxides and also, where appropriate, their pharmaceutically-acceptable addition salts with an acid or a base.

The present invention extends also to a process for the preparation of compounds of formula (I) which is characterised in that anthranilic acid is reacted in the presence of a metal chloride, such as zinc chloride, in an anhydrous alcoholic solvent, for example butanol, at reflux, with the compound of formula (II):

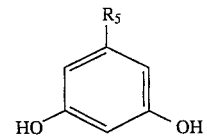

wherein $R_5$ is as defined above,
to form the compound of formula (III):

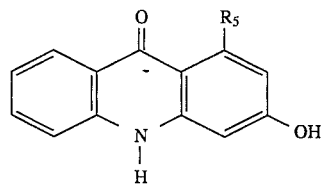

wherein $R_5$ is as defined above,
which is then treated with an alkyne of formula (IV):

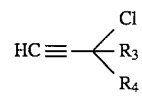

wherein $R_3$ and $R_4$ are as defined above,
in an aprotic solvent, such as dimethylformamide, at reflux, in the presence of an alkali metal carbonate, such as potassium carbonate, to yield the compound of formula ($V_1$):

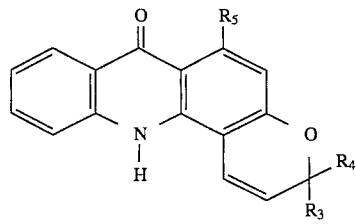

wherein $R_3$, $R_4$ and $R_5$ are as defined above,
the nitrogen atom of which is optionally substituted, by the action of an alkyl halide or a dialkyl sulfate in the presence of a deprotonation agent, such as sodium hydride, in a polar aprotic solvent, for example dimethylformamide, so as to obtain the compound of formula $(V_2)$:

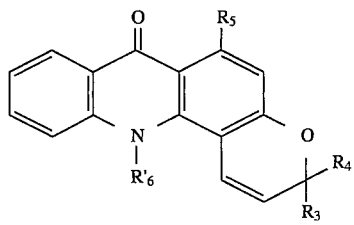

wherein $R_3$, $R_4$, $R_5$ are as defined above and $R'_6$ is identical to $R_6$ defined above, with the exception of hydrogen, the compound of formula $(V_1)$ or the compound of formula $(V_2)$ then being subjected to the action of osmium tetroxide in an appropriate solvent, such as a tert-butanol/tetrahydrofuran/water mixture, in order to obtain the vicinal cis-diol of formula (VI):

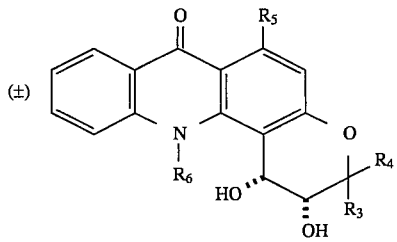

wherein $R_3$, $R_4$, $R_5$ and $R_6$ are as defined above, which is subjected:

A/ to the action of N,N'-carbonyldiimidazole so as to obtain the compound of formula (I/A):

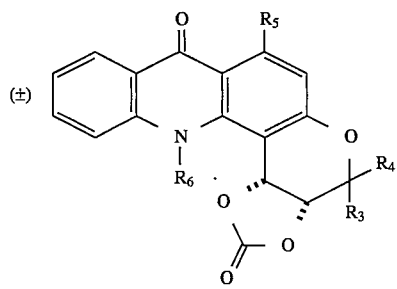

wherein $R_3$, $R_4$, $R_5$ and $R_6$ are as defined above,

B/ or to the action of a compound of formula (VIIa) or (VIIb):

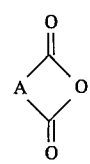

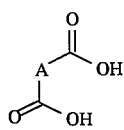

wherein A is as defined above, to obtain the compound of formula (I/B):

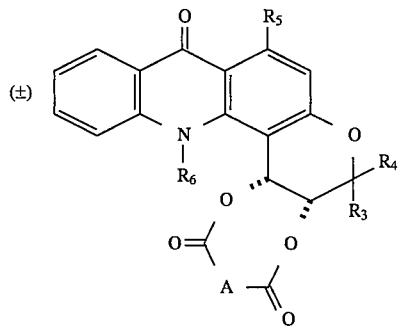

wherein $R_3$, $R_4$, $R_5$, $R_6$ and A are as defined above,

C/ or to the action of an alcohol of formula $R_1$-OH wherein $R_1$ is as defined above, in the presence of an acid, such as hydrogen chloride, so as to obtain the compound of formula (VIII):

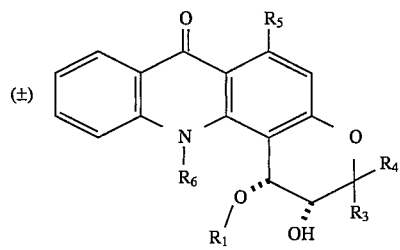

wherein $R_1$, $R_3$, $R_4$, $R_5$ and $R_6$ are as defined above, the free alcohol function of which is esterified in the presence of a weak base, such as pyridine, by the anhydride of formula $(R_2CO)_2O$, wherein $R_2$ is as defined above, to yield the compound of formula (I/C):

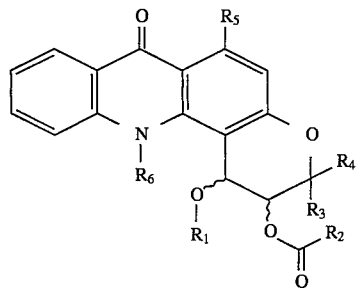

wherein $R_1$, $R_2$, $R_3$, $R_4$, $R_5$ and $R_6$ are as defined above,

D/ or directly to the action of the anhydride of formula $(R_2CO)_2O$ under the same operating conditions as those described in paragraph C/, in order to obtain the compound of formula (I/D):

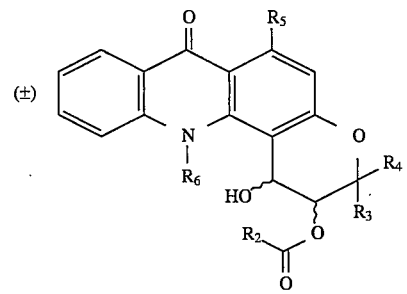

wherein $R_2$, $R_3$, $R_4$, $R_5$ and $R_6$ are as defined above, which may be subjected, under the same operating conditions, to the action of the anhydride of formula $(R_1CO)_2O$ to yield the compound of formula (I/E):

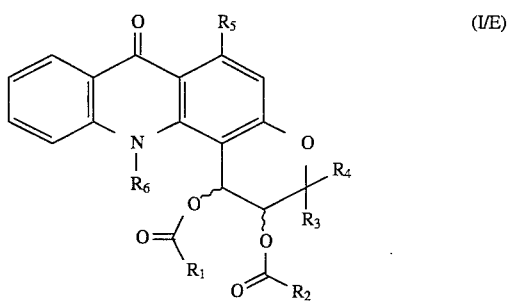

wherein $R_1$, $R_2$, $R_3$, $R_4$, $R_5$ and $R_6$ are as defined above, the totality of the compounds of formulae (I/A) to (I/E) forming the totality of the compounds of formula (I), which are purified and where appropriate separated into their enantiomers and diastereoisomers by a conventional method of separation, optionally converted into their N-oxides and, where appropriate, into their pharmaceutically-acceptable addition salts with an acid or a base.

The compound of formula (I) wherein X and Y are identical and represent the group

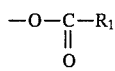

may be obtained directly by the action of the anhydride of formula $(R_1CO)_2O$ on the diol of formula (VI).

The compounds of formula (VI) wherein $R_3=R_4=CH_3$ may advantageously be obtained by the direct action of osmium tetroxide on acronycine ($R_5$=OMe and $R_6$=Me), on 6-demethoxyacronycine ($R_5$=H and $R_6$=Me), on 6-O-demethylacronycine ($R_5$=OH and $R_6$=Me) or on N-demethyl-6-O-demethylacronycine ($R_5$=OH and $R_6$=H).

The compounds of the invention, like acronycine, exhibit particularly valuable anti-tumour properties. These new compounds have furthermore proved far more active and more powerful than the reference compound. In addition they are soluble and thus allow administration by the intravenous route.

In the present invention the Applicant proposes the utilisation of the anti-tumour properties of acronycine by the production of new analogues that can be used therapeutically. The pharmacological studies presented in the following Examples show the very great value of the new compounds of the invention in the treatment of various tumours both in vitro and in vivo.

The present invention relates also to pharmaceutical compositions containing a compound of formula (I), or one of its N-oxides or pharmaceutically-acceptable addition salts with an acid or a base, alone or in combination with one or more inert, non-toxic excipients. Among the pharmaceutical compositions according to the invention there may be mentioned more especially those which are suitable for oral, parenteral, nasal, rectal, perlingual, ocular or pulmonary administration, and especially injectable preparations, aerosols, eye or nose drops, tablets, dragées or film-coated tablets, soft gelatin capsules, hard gelatin capsules, suppositories, creams, ointments, dermal gels. . .

The dosage varies in accordance with the age and weight of the patient, the administration route, the nature of the disorder and possible associated treatments, and ranges from 0.2 mg to 2 g per 24 hours.

The following Examples illustrate the invention without limiting it in any way. The starting materials are known or are prepared by known methods of operation.

Preparation A:
(±)-cis-1,2-dihydroxy-1,2-dihydro-acronycine 3.21 g (10 mmol) of acronycine are added to a mixture of a 2.5% osmium tetroxide solution in 6.4 ml of 2-methyl-propan-2-ol and 1.68 g (11 mmol) of N-methylmorpholine N-oxide dihydrate in 45 ml of a tert-butanol/tetrahydrofuran/water mixture (10:3:1). The reaction mixture is stirred at room temperature for 2 days. 120 ml of a saturated sodium hydrogen sulfate solution are then added. After stirring for one hour at room temperature, the reaction mixture is extracted 5 times with 80 ml of methylene chloride each time. Customary treatment of the organic phase yields 4 g of a residue which, after purification by flash chromatography on silica (eluant: methylene chloride/methanol, 98:2 to 95:5), gives 2.66 g (7.5 mmol) of the expected product.

Yield: 75%

Spectral characteristics: Infra-red (KBr): ν max $(cm^{-1})$: 3400, 2920, 1650, 1600, 1585, 1390, 1095

Preparation B: (±)-cis-1,2-dihydroxy-1,2-dihydro-6-demethoxy-acronycine

This compound was prepared in accordance with the method of operation described in Preparation A, from 6-demethoxy-acronycine.

Yield: 65%

Spectral characteristics: Infra-red (KBr): ν max $(cm^{-1})$: 3450, 3290, 3005, 3000, 2985, 1605, 1555, 770, 650

Preparation C:
(±)-cis-1,2-dihydroxy-1,2-dihydro-6-O-demethylacronycine

This compound was prepared in accordance with the method of operation described in Preparation A, from 6-O-demethylacronycine.

Yield: 70%

Spectral characteristics: Infra-red (KBr): ν max $(cm^{-1})$: 3515, 3330, 3005, 2985, 1685, 1595, 1155, 840, 772

Preparation D:
(±)-cis-1,2-dihydroxy-1,2-dihydro-N-demethyl-6-O-demethylacronycine This compound was prepared in accordance with the method of operation described in Preparation A, from N-demethyl-6-O-demethylacronycine.

Yield: 70%

Spectral characteristics: Infra-red (KBr): ν max $(cm^{-1})$: 3500, 3310, 3005, 2980, 1690, 1615, 1490, 1345, 775

EXAMPLE 1

(±)-cis-1,2-diacetoxy-1,2-dihydro-acronycine 1.775 g (5 mmol) of the compound obtained in Preparation A are added to a previously cooled mixture of 5 ml of anhydrous pyridine and 5 ml of acetic anhydride. The mixture is stirred at room temperature for 24 hours, and is then poured onto 50 ml of ice-cold water. The precipitate formed is recovered by filtration, washed with water and then dried. 2.034 g of the expected compound are obtained.

Yield: 92%

Spectral characteristics: Infra-red (KBr): ν max $(cm^{-1})$: 3000, 2950, 2870, 1752, 1639, 1590, 1505, 1245, 1160, 772

EXAMPLE 2

(±)-cis-1,2-diacetoxy-1,2-dihydro-6-demethoxy-acronycine

This compound was prepared in accordance with the method of operation described in Example 1, from the compound obtained in Preparation B.

Yield: 91%

Spectral characteristics: Infra-red (KBr): ν max (cm$^{-1}$): 3010, 3000, 2970, 1738, 1625, 1595, 1230, 765, 645

EXAMPLE 3

(±)-trans-1,2-dibenzoyloxy-1,2-dihydro-acronycine 0.178 g (0.5 mmol) of the compound obtained in Preparation A are dissolved in 3 ml of anhydrous pyridine, then treated with 1 g (4 mmol) of benzoic anhydride. The mixture is stirred at room temperature for 36 hours, then evaporated to dryness without heating. The residue is subjected to chromatography on silica (eluant: ethyl acetate/toluene, 70:30), yielding 0.0281 g of the expected compound accompanied by the compounds described in the following Examples 4 and 5.

Yield: 10%

Spectral characteristics: Infra-red (KBr): ν max (cm$^{-1}$): 3100, 3000, 2890, 2795, 1740, 1630, 1270, 1220, 1000, 770, 720

EXAMPLE 4

(±)-cis-1,2-dibenzoyloxy-1,2-dihydro-acronycine

This compound is obtained in the course of the purification by chromatography on a silica column of the crude product obtained in Example 3.

Yield: 7.5%

Spectral Characteristics: Infra-red (KBr): ν max (cm$^{-1}$): 3100, 3000, 2890, 2795, 1740, 1630, 1270, 1220, 1000, 770, 720

EXAMPLE 5

(±)-cis-2-benzoyloxy-1-hydroxy-1,2-dihydro-acronycine

This compound is obtained in the course of the purification by chromatography on a silica column of the crude product obtained in Example 3.

Yield: 40%

Spectral characteristics: Infra-red (KBr): ν max (cm$^{-1}$): 3350, 3100, 3000, 2795, 1720, 1630, 1600, 1270, 1220, 770, 720

EXAMPLE 6

(±)-cis-1-acetoxy-2-benzoyloxy-1,2-dihydro-acronycine 0.092 g (0.2 mmol) of the compound obtained in Example 5 are added to a pre-cooled mixture of 2.5 ml of anhydrous pyridine and 2.5 ml of acetic anhydride. The mixture is stirred at room temperature for 48 hours, then evaporated to dryness under reduced pressure without heating. The residue is subjected to purification by chromatography on a silica column (eluant: methylene chloride), yielding 0.1 g of the expected compound.

Yield: 95%

Spectral characteristics: Infra-red (KBr): ν max (cm$^{-1}$): 3100, 3005, 2980, 1730, 1630, 1600, 1285, 1225, 770, 720

EXAMPLE 7

(±)-cis-1,2-carbonyldioxy-1,2-dihydro-acronycine 1.62 g (10 mmol) of N,N'-carbonyldiimidazole are added to a solution of 0.710 g (2 mmol) of the compound obtained in Preparation A in 50 ml of butan-2one. The whole is heated at reflux for 3 hours under argon, then taken up in a 5% aqueous sodium carbonate solution (60 ml) and subsequently extracted 3 times with 40 ml of ethyl acetate each time. Customary treatment of the organic phase yields a crude product which, after crystallisation in methylene chloride, results in 0.5 g of the expected compound.

Yield: 65.5%

Spectral characteristics: Infra-red (KBr): ν max (cm$^{-1}$): 3015, 3000, 2990, 1805, 1635, 1610, 1590, 770, 710

EXAMPLE 8

(±)-trans-2-acetoxy-1-methoxy-dihydro-acronycine 1 ml of a methanolic solution saturated with gaseous hydrogen chloride is added at 0° C. to a solution of 0.175 g (0.5 mmol) of the compound obtained in Preparation A in 10 ml of methanol. The mixture is stirred for 48 hours at room temperature, neutralised by the addition of an Amberlite resin IR 50 OH, then filtered and evaporated under reduced pressure. The residue obtained, which mainly consists of (±)-cis/trans-2-hydroxy-1-methoxy-1,2-dihydroacronycine, is acetylated by a mixture of 2 ml of anhydrous pyridine and 2 ml of acetic anhydride. The reaction mixture is stirred at room temperature for 48 hours, then evaporated to dryness under reduced pressure without heating. The residue is subjected to purification by chromatography on a silica column (eluant: cyclohexane/ethyl acetate, 70:30 to 50:50), yielding 0.042 g of the expected compound as well as 0.040 g of the compound described in Example 9.

Total yield: 40%

EXAMPLE 9

(±)-cis-2-acetoxy-1-methoxy-1,2-dihydro-acronycine

This compound is obtained during the course of the purification of the crude product described in Example 8.

PHARMACOLOGICAL STUDY

Example A: Activity in vitro

A cell line, murine leukaemia L1210, was used. The cells are cultivated in a complete culture medium RPMI 1640, containing 10% foetal calf serum, 2 mM glutamine, 50 units/ml penicillin, 50 mg/ml streptomycin and 10 mM Hepes, pH: 7.4. The cells are distributed on microplates and exposed to the cytotoxic compounds for four doubling periods, that is 48 hours. The number of viable cells is then quantified by a colorimetric assay, the Microculture Tetrazolium Assay (J. Carmichael et al., *Cancer Res.*, 47, 936–942, (1987)). The results are expressed as IC$_{50}$, the concentration of cytotoxic agent that inhibits the proliferation of treated cells by 50%. The results obtained are listed in Table 1.

TABLE 1

| Cytotoxicity for L1210 cells in culture | |
|---|---|
| Compounds | Cytotoxicity IC$_{50}$ μM |
| Example 1 | 4.9 |
| Example 3 | 3.4 |
| Example 5 | 7.1 |
| Example 6 | 5.0 |
| Example 7 | 0.2 |
| acronycine | 27.0 |

All of the compounds of the invention are far more powerful than the reference compound (acronycine).

Example B: Activity in vivo

In this Example, the compounds were suspended in Tween 80, then diluted with water. The concentration of Tween is at a maximum of 1% at the strongest doses. The control animals received the carrier only.

B-1/ Anti-tumour activity against the line P388

Line P388 (murine leukaemia) was supplied by the National Cancer Institute (Frederick, U.S.A.). The tumour cells (10$^6$ cells) were inoculated on day 0 into the peritoneal cavity of female B6D2F1 mice (Iffa-Credo, France). Eight to ten mice, of a weight ranging from 18 to 20 g, were used for each experimental group. The compounds were administered via the intraperitoneal route on day 1 or once a day for 4 days (D1–4), and by the intravenous route on day 1.

The anti-tumour activity is expressed as a T/C %:

$$T/C \% \text{ (mice)} = \frac{\text{Median survival time of treated animals}}{\text{Median survival time of control animals}} \times 100$$

Table 2 indicates the anti-tumour activity achieved at the optimum doses for each scheme and administration route.

TABLE 2

| Anti-tumour activity against line P388 | | | | |
|---|---|---|---|---|
| Compound | Scheme | Route | Optimum dose (mg/kg) | T/C % (survival) |
| acronycine | D1 | i.p. | 200 | 125 |
|  | D1-4 | i.p. | 100 | 136 |
| Example 1 | D1 | i.p. | 25 | 289 |
|  | D1-4 | i.p. | 12.5 | 172 |
|  | D1 | i.v. | 25 | 220 |
| Example 5 | D1 | i.p. | 12.5 | 258 |
| Example 7 | D1 | i.p. | 50 | 269 |

The compounds are very active against that tumour, the compound of Example 1 being extremely active by the i.p. and i.v. routes. Acronycine has weak activity by the i.p. route, and at far stronger doses. Acronycine, which is completely insoluble, cannot be tested by the i.v. route.

B-2/ Anti-tumour activity of the compounds against colon 38

Colon 38 (supplied by NCI, Frederick, U.S.A.) was inserted in the form of fragments by the subcutaneous route (s.c.) into female B6D2F1 mice. The compounds were administered by the i.p. route on D2 and D9 and the anti-tumour activity was determined on D21 by measuring the rumour volume (T/C volume, %).

$$T/C \% \text{ (volume)} = \frac{\text{Median tumour volume of treated animals}}{\text{Median tumour volume of control animals}} \times 100$$

The results are listed in the following Table 3:

TABLE 3

| Anti-tumour activity of the compounds against colon 38 | | | | |
|---|---|---|---|---|
| Compound | Scheme | Route | Dose (mg/kg) | median T/C % (tumour volume on D21) |
| acronycine | D2,9 | i.p. | 100 | 77 |
|  |  |  | 200 | 61 |
| Example 1 | D2,9 | i.p. | 6.25 | 12 |
|  |  |  | 12.5 | 8 |
|  |  |  | 25 | 1 |
| 5-fluoro-uracil | D2,9 | i.p. | 80 | 0 |

The compound of Example 1 is very active against that very resistant solid tumour and is as active at 25 mg/kg as 5-fluoro-uracil (reference molecule in this model, used clinically) is at 80 mg/kg.

B-3/ Xenograft HT-29 in hairless mice

HT-29 tumour cells originating from a human colon adenocarcinoma (American Type Culture Collection, U.S.A.) are inoculated by the subcutaneous route into hairless female mice (Iffa Credo, France). The tumour is then amplified by successive passages of tumour fragments of 2–3 mm$^3$ implanted bilaterally by the subcutaneous route in the animals' flanks. When the tumour has reached a size of 50 mm$^3$ (that is between 7 and 10 days after the graft), the animals are randomised into groups of 7 to 10 mice and treated in accordance with the protocol indicated. The animals are weighed and their tumour is measured twice a week.

The tumour volume is calculated in accordance with the following formula:

$$Vt = \frac{a \cdot b^2}{2}$$

$a$ = tumour lenght
$b$ = tumour width

The results are expressed as the median relative tumour volume:

$$\frac{\text{median } Vt \text{ at time } t \, (V_t)}{\text{median } Vt \text{ at time } 0 \, (V_0)}$$

The anti-tumour activity of the compound administered is evaluated by the minimum value of the median T/C calculated at time t:

$$\text{median } T/C \% \text{ (volume)} = \frac{(V_t/V_o) \text{ treated group}}{(V_t/V_o) \text{ control group}} \times 100$$

The minimum value of this parameter is evaluated a minimum of 7 days after the last treatment in accordance with EORTC (European Organization for the Treatment of Cancer) standards.

The animals are treated by the i.p. route by weekly administration for 2 weeks of the compound of Example 1. D0 corresponds to the first time the tumours are measured and the first administration of compound.

The compound of Example 1 is active against that very resistant tumour. Table 4 shows the best T/C.

TABLE 4

Activity of the compound of Example 1 against an HT-29 tumour implanted in hairless mice

| Compound | Dose (mg/kg) | Scheme | Δ weight (g) (D10-D0) | Minimum median T/C % (day) | Antitumour effect |
|---|---|---|---|---|---|
| Example 1 | 6.25 | D0,7 | −1.1 | 46 (D32) | + |
| Control | — | — | 0 | 100 | |

Example C: Pharmaceutical composition: Tablets
Preparation formula for 1000 20 mg tablets

| | |
|---|---|
| Example 1 compound | 20 g |
| Lactose | 40 g |
| Magnesium stearate | 10 g |
| Corn starch | 15 g |
| Wheat starch | 15 g |
| Silica | 5 g |
| Hydroxypropylcellulose | 5 g |

We claim:

1. A compound of formula (I):

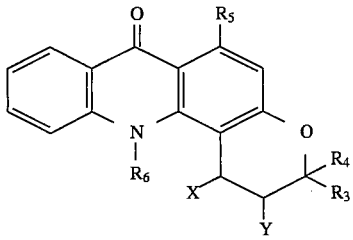

wherein:

X represents $-O-R'_1$ and Y represents

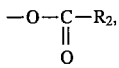

or X represents

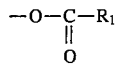

and Y represents

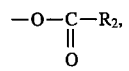

$R_1$ and $R_2$, which are the same or different, each represents, independently of the other, phenyl or a hydrocarbon radical having 1 to 6 carbon atoms inclusive in straight or branched chain and being optionally monosubstituted by a group selected from hydroxy, halogen, nitro, amino, alkoxy, and acyl, $R'_1$ is selected from hydrogen and $R_1$, A is selected from a valency bond and a divalent hydrocarbon group optionally having one or more unsaturations and having 1 to 6 carbon atoms inclusive in straight or branched chain, and which is optionally monosubstituted by a group selected from hydroxy, halogen, nitro, amino, alkoxy, and acyl, $R_3$, $R_4$ and $R_6$, which are the same or different, are each selected, independently of the others, from hydrogen and alkyl, but $R_3$ and $R_4$ possibly being only straight-chain alkyl, $R_5$ is selected from hydrogen, hydroxy, and alkoxy, the terms "alkyl", "alkoxy" and "acyl" unless otherwise restricted being understood to designate groups having 1 to 6 carbon atoms inclusive in straight or branched chain or benzoyl, and which are optionally monosubstituted by a group selected from hydroxy, halogen, nitro, amino, alkoxy, and acyl, its possible enantiomers, diastereoisomers, N-oxides or, where appropriate, its pharmaceutically-acceptable addition salts with an acid.

2. A compound according to claim 1, wherein each of $R_3$ and $R_4$ represents methyl, its possible enantiomers, diastereoisomers, N-oxides or, where appropriate, its pharmacologically-acceptable addition salts with an acid.

3. A compound according to claim 1, which is 1,2-diacetoxy-1,2-dihydroacronycine, its enantiomers, diastereoisomers, N-oxides or, where appropriate, its pharmaceutically-acceptable addition salts with an acid.

4. A method for treating a mammal afflicted with a disease susceptible to treatment with acronycine comprising the step of administering to said mammal an amount of a compound of claim 1 which is effective for alleviation of said disease.

5. A pharmaceutical composition useful as an antitumor agent comprising an effective amount of a compound as claimed in claim 1, together with a pharmaceutically-acceptable excipient.

* * * * *

UNITED STATES PATENT AND TRADEMARK OFFICE
CERTIFICATE OF CORRECTION

PATENT NO. : 5,567,707
DATED : Oct. 22, 1996
INVENTOR(S) : M. Koch; F. Tillequin; A.L. Skaltsounis; Y. Rolland; A. Pierre; G. Atassi It is certified that error appears in the above-indentified patent and that said Letters Patent is hereby corrected as shown below:

Column 6, linie 18: "$(cm^{-1)}:$" should read -- $(cm^{-1})$: --.

Column 12, line 5: Insert below the formula -- or X and Y together form the group $-O-C-A-C-O-$,
$$\underset{O}{\overset{\parallel}{\phantom{C}}}\quad\underset{O}{\overset{\parallel}{\phantom{C}}}$$
--.

Column 12, line 8: Insert, before "$R_1$", -- wherein --. after line 7:.

Column 12, 41: Insert -- an -- before "acronycine" and insert -- anti-tumour agent -- after "acronycine.

Signed and Sealed this

Fourteenth Day of January, 1997

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,567,707
DATED : Oct. 22, 1996
INVENTOR(S) : M. Koch; F. Tillequin; A.L. Skaltsounis; Y. Rolland; A. Pierre; G. Atassi It is certified that error appears in the above-indentified patent and that said Letters Patent is hereby corrected as shown below:

Column 6, linie 18: "($cm^{-1}$):" should read -- ($cm^{-1}$): --.

Column 12, line 5: Insert below the formula -- or X and Y together form the group -O-C-A-C-O-,  --.

Column 12, line 8: Insert, before "R$_1$", -- wherein --.

after line 7:.

Column 12, 41: Insert -- an -- <u>before</u> "acronycine" and insert -- anti-tumour agent -- <u>after</u> "acronycine.

This certificate supersedes Certificate of Correction issued January 14, 1997.

Signed and Sealed this

Twenty-ninth Day of April, 1997

Attest:

BRUCE LEHMAN

Attesting Officer     Commissioner of Patents and Trademarks